United States Patent [19]

Viegas et al.

[11] Patent Number: 4,662,364

[45] Date of Patent: May 5, 1987

[54] METHOD AND BRACE TO IMMOBILIZE FRACTURES

[75] Inventors: Steven F. Viegas; Allan F. Tencer; Peggy Woodard, all of Galveston; Sue Gaynor, Kemah, all of Tex.

[73] Assignee: Board of Regents, The University of Texas System, Austin, Tex.

[21] Appl. No.: 719,071

[22] Filed: Apr. 2, 1985

[51] Int. Cl.$^4$ .............................................. A61F 5/04
[52] U.S. Cl. ...................................... 128/87 R; 128/77
[58] Field of Search ................. 128/87 R, 87 A, 89 R, 128/90, 83, 84 C, 85, 77

[56] References Cited

U.S. PATENT DOCUMENTS

| | | | |
|---|---|---|---|
| 2,529,786 | 11/1950 | Shaw | 128/89 R |
| 2,692,594 | 10/1954 | Kelly | 128/87 R |
| 3,124,127 | 3/1964 | Ruuska | 128/89 R |
| 3,299,888 | 1/1967 | Muckinhaupt | 128/87 R |
| 3,788,307 | 1/1974 | Kistner | 128/87 R |
| 4,294,237 | 10/1981 | Frazier | 128/87 A |

Primary Examiner—Gene Mancene
Assistant Examiner—C. W. Shedd
Attorney, Agent, or Firm—Arnold, White & Durkee

[57] ABSTRACT

An adjustable brace and method for reducing and immobilizing a bone fracture, which includes adjustable pads, and allows the physician to precisely apply pressure in the desired area of the fracture. The preferred brace is particularly designed for immobilizing metacarpal fractures in the hand by applying three point pressure in the area of the metacarpal fracture while allowing essentially full movement of the wrist, hand and fingers. Thus, the hand brace is preferable to conventional casts or splints in allowing more normal movement. Further, the brace is generally radiolucent to more readily monitor the healing of the fracture radiographically. The hand brace preferably includes: a U-shaped bracket with the bight portion fitted in the first web space of the hand; a top, flat, elongated member adjoining the back of the hand; and, a bottom, flat, elongated member received in the palm. A pair of spaced apart pads are positioned in the palm facing the general area of fracture. Another pad is connected to the top member facing the back of the hand in the general area of the fracture. The free ends of the brace are connected by a strap for drawing the members together. The pads are positioned relative each other such that with the strap tightened, three point pressure is applied to reduce and immobilize the fracture.

18 Claims, 4 Drawing Figures

METHOD AND BRACE TO IMMOBILIZE FRACTURES

BACKGROUND OF THE INVENTION

1. Field of the Invention

This invention relates to a brace and method for immobilizing a fracture which allows the physician to adjustably position the pressure applied by the brace to more effectively reduce and immobilize the fracture. More particularly, the preferred brace of the present invention is designed to treat fractures in the hand, while allowing movement of the fingers and the wrist.

2. Description of the Prior Art

Approximately one-half of all accidents involve fractures in the hand or fingers. Fractures in the bones of the hand comprise approximately one-third of all fractures. The most frequent hand fracture involves the metacarpal, particularly the fifth metacarpal or a so called "boxer's fracture". Typical metacarpal deformity involves apex dorsal angulation. Since the metacarpal is somewhat superficial, the deformity takes the form of a bump on the dorsam of the hand and loss of the metacarpal head definition. The resulting prominence of the metacarpal head in the palm can cause discomfort, particularly in an individual who must grip tools or do heavy manual labor in his chosen profession.

Previous studies of hand fractures have suggested that angulation of the fracture up to 40° was acceptable without even attempting reduction of the fracture. Further, these studies suggest that if reduction could not easily be performed under a local anesthesia, angulation up to 70° was acceptable provided there was not excessive rotation of a distal fragment. Additionally, these studies suggested that angulation up to 70° was acceptable if the reduction could not be readily maintained.

More recent studies and text books reference patient dissatisfaction cosmetically, symptomatically and functionally with this degree of deformity. Today the maximum acceptable angular deformity is around 30° in the fifth metacarpal, to only 10°–15° in the second and third metacarpal bones.

There are many types of treatment, reduction, and immobilization for metacarpal fractures. These include the use of casts, splints and mechanical devices to achieve the reduction and immobilization. The most common treatment of metacarpal fractures involves the use of an ulnar gutter plaster splint which immobilizes the wrist and certain fingers, depending upon the location of the metacarpal fracture.

There are a number of deficiencies in the use of such casts and splints in the treatment of fractures, particularly metacarpal fractures of the hand. Conventional casts and splints immobilize the fingers, wrists, and to some extent the forearm, which effectively prevents most use of the hand by the patient. Further, conventional casts and splints not only shield the area of the fracture from visual inspection, but additionally substantially degrades the quality of radiographs for monitoring the healing of the fracture.

Further, such conventional casts and splints are not always effective in applying the appropriate amount of pressure at the appropriate locations for a given fracture, particularly a metacarpal fracture. That is, even assuming that proper reduction can initially be made within acceptable angulation limits, there is risk of shifting and rotation of the fracture outside of acceptable angulation limits, in part due to inappropriate pressure. When coupled with the difficulties in visual and radiographic inspection of the fracture reduction, it is readily apparent that conventional casts and splints are lacking in many respects in the treatment of fractures, particularly metacarpal fractures. Therefore, it would be a significant advance in the art if a method and device were devised that the physician could readily adapt to provide the appropriate pressure to a fracture to achieve the desired reduction and immobilization. Further, a device which was inexpensive, permitted visual inspection, and was radiolucent, would be highly desirable in the treatment of fractures, particularly, hand fractures such as metacarpal fractures.

SUMMARY OF THE INVENTION

The problems outlined above are in large measure solved by the brace of the present invention. That is to say, the brace hereof is easily adjustable by the physician to provide the appropriate pressure to a fracture in a desired location to reduce and maintain the reduction and to immobilize the fracture. Further, the brace hereof is inexpensive, easy to use, permits visual inspection of the area surrounding the fracture, and is radiolucent. Finally, the hand brace of the preferred embodiment is particularly effective for treating metacarpal fractures and allows movement of the fingers, wrist and hand while maintaining the desired reduction and immobilization of the metacarpal fracture.

Broadly speaking, the brace of the present invention includes first and second elongated members adapted for positioning on each side of the fracture, and first and second pressure mechanisms operably couplable to the respective members. One of the mechanisms includes at least one pad ("apex pad") while the other pressure mechanism includes at least a pair of spaced apart pads ("base pads"). The brace includes connecting means which operates to draw the members towards each other. Advantageously, an apex pad and two of the base pads are adjustably positioned on the members on each side of the fracture generally in a dihedral orientation, such that drawing the members towards each other applies a three-point pressure effectively reducing and immobilizing the fracture. Although the brace of the present invention is easily adaptable for practically any type of fracture with the attendant advantages as outlined above, it is particularly suited for metacarpal fractures of the hand as illustrated in the non-limiting preferred embodiment described herein.

Preferably, the brace designed for treating metacarpal fractures of the hand includes a U-shaped bracket having an upper member adapted for adjoining the back of the hand, and a lower member adapted for reception in the palm region of the hand. A semi-rigid bight portion connects the distal ends of the generally parallel members, and is adapted for reception in the first web space between the thumb and the index finger. The brace also includes a base pressure mechanism comprising an elongated bar having two spaced apart pads mounted thereon. The bar is adjustably fastenable on the lower member adjoining the palm of the hand in the appropriate region of the fracture. An apex pad is adjustably fastenable on the upper member adjoining the back of the hand.

Depending upon the location and nature of the fracture, the base and apex pads can be positioned by the physician adjacent the desired pressure points. The free ends of the members are joined by an adjustable strap, allowing the physician to adjust the amount of pressure applied by the pads in the region of the fracture. Although the invention contemplates two pressure points on one side of the fracture and a third pressure point on the other side of the fracture with the pads arranged in a dihedral relationship, it will be appreciated that a plurality of pads can be incorporated if desired.

The brace designed for metacarpal fractures of the hand is particularly advantageous in that it is easily adjustable for use with most types of metacarpal fractures. That is, the brace adjusts for use with fractures of the fifth, fourth, third, or second metacarpals. Further, the hand brace can be used with either the left or right hand, and is adjustable to accommodate different hand sizes. Finally, metacarpal fractures occur with varying degrees of obliquity and severity; the adjustable pads allow the physician to easily treat these variations.

DESCRIPTION OF THE PREFERRED EMBODIMENT

Figure 1:
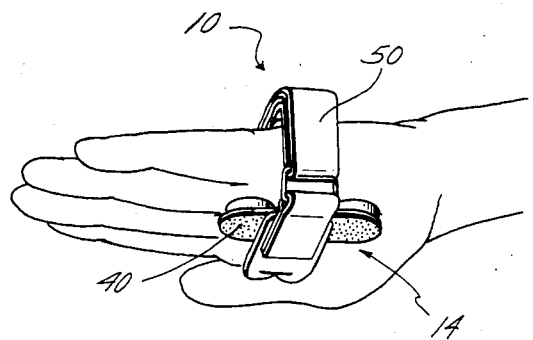
FIG. 1 is a perspective view of a brace in accordance with the present invention shown in operative engagement with a hand.

Turning now to the drawing, a brace 10 in accordance with the present invention is illustrated as applied to a fifth metacarpal fracture of the left hand. Generally speaking, the brace 10 includes a U-shaped bracket having generally flat, parallel, elongated members 12, 14; pressure mechanisms 16, 18; and connecting means 20 operable for drawing the members 12, 14 towards each other.

Preferably, the members 12, 14 are oriented generally parallel with adjacent ends connected by the bight portion 22. As seen in FIG. 2, the bight portion 22 is arranged to fit comfortably in the first web space between the index finger and thumb of the hand. Alternatively, the brace 10 can be applied with the bight portion 22 adjacent to the ulnar aspect of the hand to provide another method of immobilizing the second or third metacarpal. As shown in the drawing, the upper member 12 is adapted to fit over the back of the hand region, while the lower member 14 (FIG. 1) is received adjacent the palm portion of the hand.

Figure 3:
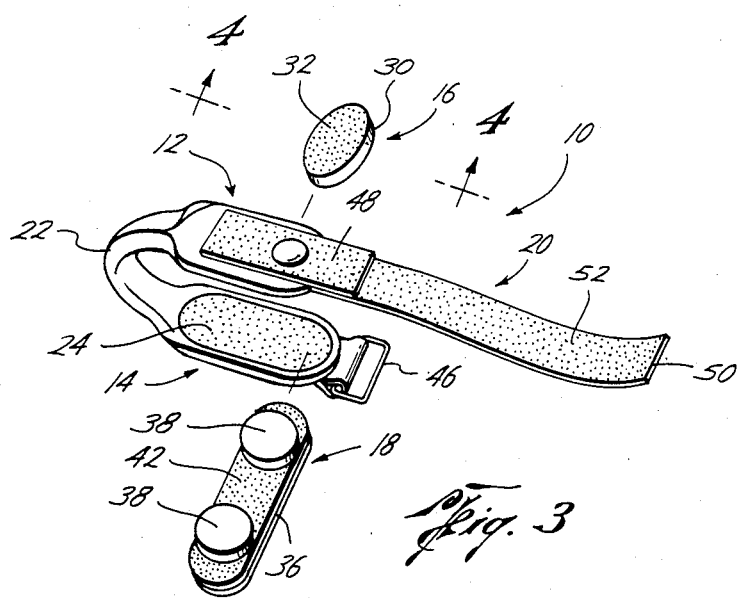
FIG. 3 is a perspective, partially exploded view of the brace of the present invention.

Advantageously, structure is provided for adjustably coupling the pressure mechanisms 16, 18 to the respective members 12, 14 (FIG. 3). To this end, the flat, inboard surfaces of the members 12, 14 present the hook portion 24 of a conventional hook and pile fastening system (such as VELCRO).

Figure 2:
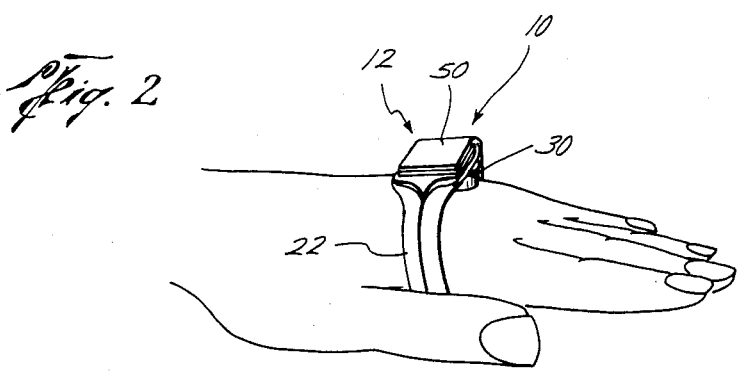
FIG. 2 is a perspective view of the brace of FIG. 1 from another angle.
Figure 4:
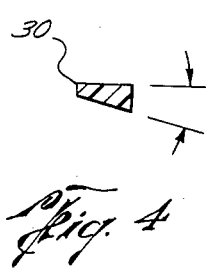
FIG. 4 is a sectional view of the apex pad taken along line 4—4 of FIG. 3. de

In the preferred embodiment shown in the drawing, the pressure mechanism 16 simply incorporates a single apex pad 30 having a pile surface 32 as shown in FIG. 1. Thus, the apex pad 30 is adjustably couplable to the member 12 by the interconnection of the pile surface 32 and complemental hook surface 24. The other surface of the apex pad 30 is obliquely angled as shown in FIG. 4, to comfortably interface with the curved portion of the back of the hand as shown in FIG. 2.

The pressure mechanism 18 includes an elongated, generally flat bar 36 and a pair of spaced-apart base pads 38 as shown in FIG. 3. One side of the bar 36 has a pile surface 40 (FIG. 1) permitting adjustable positioning on the hook surface 24 of the member 14 shown in FIG. 3. The other side of the bar 36, has a hook surface, as at 42, while the respective base pads 38 have complemental pile surfaces (not shown) for adjustably mounting the base pads 38 along the surface 42 (FIG. 3).

The connecting means 20 incorporates a metal D ring 46 connected to the free end of the member 14 as shown in FIG. 3. The upper surface 48 of the member 12 has a complemental hook structure. An elongated strap 50 is secured to the free end of the member 12 (remote from bight 22). Strap 50 includes an in-board pile surface 52 as shown in FIG. 3. The strap 50 is adapted for interfitting through the D ring 46 with adjustable attachment provided between the hook and pile surfaces 48, 52 (compare FIGS. 3, 1).

Although fifth metacarpal fractures are the most commonly occurring, fractures in the second, third, and fourth metacarpals frequently occur as well. Further, many different severities and orientations of the fractures are possible. The brace 10 of the present invention is advantageous in allowing the attending physician to easily adapt the brace 10 to treat the particular bone and type fracture. FIGS. 1 and 2 illustrates the brace 10 when immobilizing a fifth metacarpal fracture. Further, analysis of FIG. 3 reveals that the brace 10 can be utilized with either the left or the right hand.

To apply the brace, the physician interfits the bight portion 22 in the first web space of the hand with the strap 50 unconnected. Depending upon the location and alignment of the break, the physician orientates the pads 30, 38 as desired. That is, pads 38 are adjustably spaced apart on the bar 36 and the bar 36 attached to the member 14 as shown in FIG. 1. The apex pad 30 is positioned on the member 12 adjacent the fracture as shown in FIG. 2. The pads 30, 38 are thus positioned in a generally dihedral relationship, with the pads being generally coplanar while pad 30 is positioned on the other side of the hand, but between the base pads 38.

The strap 50 is interfitted through the D ring 46 and tightened as desired, with the pile surface 52 connected to the upper hook surface 48. It will be appreciated that tightening of the strap 50 draws the members 12, 14 (and the pads 30, 38) towards each other applying a compressing force on the hand in the area of the fracture. The tightening of the strap 50 is adjustable, so that the pressure applied by the pads 30, 38 can be varied as desired. The dihedral relationship yields a three point pressure with the base pads applying a vector force opposed to the vector force of the apex pad.

The tightening of the strap 50 essentially applies a 3 point pressure in the region of the hand at the desired location relative to the fracture. If the pads 30, 38 are properly positioned, tightening of the strap 50 will in most cases provide acceptable reduction of the fracture, and with the strap 50 secured, the fracture is immobilized.

With the brace 10 in its treating configuration as shown in FIGS. 1 and 2, many advantages are readily apparent over conventional reduction and immobilization methods. The biomechanical advantage which the brace 10 offers the physician fascilitates the reduction and may decrease the need for, or reduce the dose of patient analgesia during the reduction. Most of the hand is exposed which is advantageous for clinical inspection and cleanliness. Further, brace 10 is of a synthetic resin, radiolucent material which permits easy radiographic monitoring by the physician of the alignment and healing progress of the fracture. Most importantly, with the brace 10 in position, the patient has a relative large freedom of movement of the wrist, hand, and fingers, allowing most normal activities. This has several potential benefits among which are earlier return to the patient's vocation and a quicker resolution of edema.

Although the brace 10 of the preferred embodiment is designed to immobilize metacarpal fractures of the hand, those skilled in the art will appreciate that different embodiments of the present invention can easily be adapted to treat other types of fractures. Further, although only 3 pads are contemplated in the brace 10 of the preferred embodiment, it would of course be possible to incorporate a plurality of pads to accommodate certain types of comminuted or segmental fractures and multiple bone fractures.

We claim:

1. A brace for treating a fracture comprising:
   a first, elongated member adapted for positioning on one side of the fracture;
   a second, elongated member adapted for positioning on the other side of the fracture;
   first pressure mechanism operably couplable to said first member and adjustable positionable relative thereto, said first mechanism including an apex pad orientable towards the fracture;
   second pressure mechanism operably couplable to said second member and adjustably positionable relative thereto, said second mechanism including a pair of spaced-apart base pads orientable towards the fracture;
   means for adjustably coupling said first and second pressure mechanisms to the respective first and second members, said coupling means including complemental hook and pile structure attached to the members and pressure mechanisms; and
   means for connecting said first and second members on each side of the fracture with the apex pad and base pads generally positioned to present a dihedral angle, the connecting means being operable for drawing the members towards each other with the apex pad and base pads applying pressure on each side of the fracture.

2. A brace according to claim 1, said first and second members being semi-rigid.

3. A brace according to claim 1, said first member being adapted to adjoin the back of the hand and the second member being adapted to adjoin the palm.

4. A brace according to claim 1, said first and second members being generally parallel with adjacent ends connected by a semi-rigid bight portion, said bight portion being adapted for reception in the cleft of the hand between the forefinger and thumb.

5. A brace according to claim 1, said first pressure mechanism comprising only one apex pad.

6. A brace according to claim 1, said apex pad having an oblique contact surface adapted to adjoin a portion of the back of the hand.

7. A brace according to claim 1, said second pressure mechanism comprising only two base pads.

8. A brace according to claim 1 said connecting means including an adjustable strap connecting adjacent ends of respective members.

9. A brace according to claim 8, said strap having one end secured to one of the members, the other end of the strap and other member having complemental hook and pile structure for adjustable securing the other end to the other member.

10. A brace for treating a fracture comprising:
    a first, elongated member adapted for positioning on one side of the fracture;
    a second, elongated member adapted for positioning on the other side of the fracture;
    first pressure mechanism operably couplable to said first member and adjustably positionable relative thereto, said first mechanism including an apex pad orientable towards the fracture;
    second pressure mechanism operably couplable to said second member and adjustably positionable relative thereto, said second mechanism including a pair of spaced-apart base pads orientable towards the fracture;
        said second pressure mechanism comprising an elongated, flat bar, said base pads being adjustably attachable to the bar along the length thereof; and
    means for connecting said first and second members on each side of the fracture with the apex pad and base pads generally positioned to present a dihedral angle, the connecting means being operable for drawing the members towards each other with the apex pad and base pads applying pressure on each side of the fracture.

11. A brace according to claim 10, said bar being couplable to said second member in a generally transverse orientation.

12. A brace adapted for treating bone fractures in the hand which allows same freedom of movement of the wrist and fingers, comprising:
    a U-shaped bracket having generally parallel upper and lower elongated, semi-rigid members, and a rounded, semi-rigid bight portion connecting the distal ends of the members,
        the bracket being positionable on a hand with the bight portion disposed in the first web space between the thumb and index finger, the lower member received in the palm area, and the upper member adjoining the back of the hand;
    a base pressure mechanism having two or more pads mounted thereon, the base mechanism being adjustably fastenable to one of the members by a complemental hook and pile structure with the pads proximate to the hand;
    an apex pressure mechanism having at least one pad, the apex mechanism being adjustably fastenable to the other member by a complemental hook and pile structure with the one pad proximate to the hand; and
    means for connecting the free ends of the members remote from the bight portion, the connecting means being operable for compressing the members towards each other with the pads engaging the region of the hand therebetween.

13. The brace according to claim 12, wherein the base pressure mechanism includes an elongated flattened bar and means for adjustably attaching said two or more pads thereto.

14. The brace according to claim 12, said connecting means comprising a strap having one end secured to one member and means for selectively fastening the other end to the other member.

15. The brace according to claim 12, one of the apex pads and two of the base pads being positionable in a dihedral angle for applying three point, opposed pressure with the members compressed towards each other.

16. A method of immobilizing an appendage fracture comprising the steps of:
   providing a pair of elongated members each having one or more pads adjustably positionable thereon by a hook and pile structure;
   positioning the members generally on each side of the appendage proximate to the fracture;
   mounting two pads on one member with the two pads disposed in operable contact with the appendage proximate to the fracture;
   positioning one pad on the other member with said one pad in operable contact with the appendage, said one pad being positioned relative to said two pads in a general dihedral relation with the area of the fracture disposed between the one pad and the two pads; and
   compressing the members towards each other substantially immobilizing the fracture.

17. The method of claim 16, including the steps of,
   positioning the members generally in parallel,
   fastening said two pads in spaced apart relation to an elongated support bar, and
   mounting said support bar to said one member in generally transverse relation.

18. The method of claim 16, including the step of,
   reducing the fracture when the members are compressed towards each other.

* * * * *